United States Patent
Tang et al.

(10) Patent No.: US 12,367,384 B2
(45) Date of Patent: Jul. 22, 2025

(54) RESIDUAL SEMI-RECURRENT NEURAL NETWORKS

(71) Applicant: Sanofi, Paris (FR)

(72) Inventors: Qi Tang, Cambridge, MA (US); Youran Qi, Madison, WI (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/626,358

(22) Filed: Apr. 4, 2024

(65) Prior Publication Data

US 2024/0265246 A1   Aug. 8, 2024

Related U.S. Application Data

(63) Continuation of application No. 18/179,890, filed on Mar. 7, 2023, now Pat. No. 11,977,972, which is a
(Continued)

(30) Foreign Application Priority Data

May 13, 2019   (EP) ..................................... 19305611

(51) Int. Cl.
*G06N 3/063*   (2023.01)
*G01N 33/50*   (2006.01)
(Continued)

(52) U.S. Cl.
CPC ......... *G06N 3/063* (2013.01); *G01N 33/5008* (2013.01); *G06N 3/045* (2023.01); *G06N 3/082* (2013.01)

(58) Field of Classification Search
CPC ........ G06N 3/063; G06N 3/045; G06N 3/082; G06N 3/044; G01N 33/5008
(Continued)

(56) References Cited

U.S. PATENT DOCUMENTS

| | | |
|---|---|---|
| 598,744 A | 2/1898 | Perkins |
| 6,658,396 B1 | 12/2003 | Tang et al. |

(Continued)

FOREIGN PATENT DOCUMENTS

| | | |
|---|---|---|
| CN | 105335612 A | 2/2016 |
| EP | 3273373 A1 | 1/2018 |

(Continued)

OTHER PUBLICATIONS

Mohajerine, Nima; Multi-Step Prediction of Dynamic Systems with Recurrent Neural Networks; May 20, 2018; IEEE; pp. 1-13.*

(Continued)

*Primary Examiner* — Jerome Grant, II
(74) *Attorney, Agent, or Firm* — Fish & Richardson P.C.

(57) ABSTRACT

Residual semi-recurrent neural networks (RSNN) can be configured to receive both time invariant input and time variant input data to generate one or more time series predictions. The time invariant input can be processed by a multilayer perceptron of the RSNN. The output of the multilayer perceptron can be used as an initial state for a recurrent neural network unit of the RSNN. The recurrent neural network unit can also receive time invariant input, and process the time invariant input with the time invariant input to generate an output. The outputs of the multilayer perceptron and the recurrent neural network unit can be combined to generate the one or more time series predictions.

25 Claims, 5 Drawing Sheets

Related U.S. Application Data continuation of application No. 16/827,094, filed on Mar. 23, 2020, now Pat. No. 11,625,589.

(60) Provisional application No. 62/824,895, filed on Mar. 27, 2019.

(51) Int. Cl.
   *G06N 3/045* (2023.01)
   *G06N 3/082* (2023.01)

(58) Field of Classification Search
   USPC .......................................................... 706/41
   See application file for complete search history.

(56) References Cited

U.S. PATENT DOCUMENTS

| | | | |
|---|---|---|---|
| 11,625,589 B2 | 4/2023 | Tang et al. | |
| 11,977,972 B2 | 5/2024 | Tang et al. | |
| 2009/0299933 A1 | 12/2009 | Aoyama et al. | |
| 2016/0306945 A1 | 10/2016 | Jiang | |
| 2018/0253637 A1* | 9/2018 | Zhu | H04L 67/535 |
| 2019/0354836 A1* | 11/2019 | Shah | G06N 3/045 |
| 2020/0168334 A1 | 5/2020 | Mowery | |
| 2020/0311527 A1 | 10/2020 | Tang et al. | |
| 2023/0222330 A1 | 7/2023 | Tang et al. | |

FOREIGN PATENT DOCUMENTS

| | | |
|---|---|---|
| JP | 2009-288934 A | 12/2009 |
| JP | 2018-067039 A | 4/2018 |
| WO | WO 1999/058050 A1 | 11/1999 |
| WO | WO 2010/019919 A1 | 2/2010 |
| WO | WO 2018/187632 A1 | 10/2018 |

OTHER PUBLICATIONS

Camps-Valls et al., "Prediction of cyclosporine dosage in patients after kidney transplantation using neural networks," IEEE Trans Biomed. Eng., Apr. 2003, 50(4):442-448.

International Preliminary Report on Patentability in International Application No. PCT/US2020/024196, dated Sep. 28, 2021, 7 pages.

International Search Report and Written Opinion in Application No. PCT/US2020/024196, dated Jun. 18, 2020, 12 pages.

Mohajerin et al., "Multi-step prediction of dynamic systems with recurrent neural networks", IEEE Transactions on Nueral Networks and Learning Systems 30(11):3370-3383, May 20, 2018.

Soleimani et al., "Treatment-Response Models for Counterfactual Reasoning with Continuous-time, Continuous-valued Interventions," arXiv ID 1704.02038, 2007, 11 pages.

Toyoshima et al., "Automatic Evaluation of Naturalness in Topic Transitions of a Chat Dialogue System," Institute of Electronics, Information Communication Engineers, Dec. 14, 2016, 116(379):25-29 (with English translation).

Tresp et al., "Neural-network models for the blood glucose metabolism of a diabetic", IEE Transactions on Neural Networks 10(5):1204-1213, Sep. 1, 1999.

Herrero-Zazo et al., "Application of Machine Learning in Knowledge Discovery for Pharmaceutical Drug-drug Interactions," Proceedings of the 2nd International Workshop on Knowledge Discovery on the Web, Sep. 30, 2016, 12 pages.

\* cited by examiner

RESIDUAL SEMI-RECURRENT NEURAL NETWORKS

CROSS-REFERENCE TO RELATED APPLICATIONS

This application is a continuation of U.S. patent application Ser. No. 18/179,890, filed Mar. 7, 2023, which is a continuation of U.S. patent application Ser. No. 16/827,094, filed on Mar. 23, 2020, now U.S. Pat. No. 11,625,589, which claims priority to U.S. Provisional Patent Application No. 62/824,895, filed on Mar. 27, 2019, and to European Patent Application No. 19305611.6, filed May 13, 2019, the entire contents of which are incorporated herein by reference.

TECHNICAL FIELD

This disclosure relates to artificial neural networks.

BACKGROUND

Artificial neural networks (ANN) are computing systems vaguely inspired by biological neural networks. The ANN is a framework for one or more machine learning algorithms to work together and process complex data inputs. ANN's can learn to perform tasks, such as image recognition, where the ANN may learn to identify certain features within an image (e.g., animals, vehicles, road signs, etc.). An ANN typically includes a collection of connected nodes called artificial neurons. Each connection, can transmit a signal from one artificial neuron to another. An artificial neuron that receives a signal can process it and then output the result to additional artificial neurons connected to it.

In typical implementations, the signal at a connection between artificial neurons, the connection sometimes referred to as an edge, is a real number, and the output of each artificial neuron is computed in accordance with a non-linear function of the sum of its inputs. The artificial neurons and edges typically have a weight that can adjusts while the ANN is being trained. ANNs have been used for a variety of tasks, such as computer vision, speech recognition, machine translation, and medical diagnosis. Recently, ANN's have been used as prediction models for predicting a result based on some input. For example, ANN's can be used in Pharmacokinetic modeling, which predicts how a drug will interact with the human body (e.g., time course of drug absorption, distribution, metabolism, and excretion).

SUMMARY

In at least one aspect of the present disclosure a neural network is provided. The neural network includes a multi-layer perceptron (MLP) configured to receive a first type of external data and process the first type of external data to generate a MLP output. The neural network includes a recurrent neural network (RNN) unit. The RNN unit is configured to receive at least a portion of the MLP output and a second type of external data. The RNN unit is configured to process the at least a portion of the MLP output and the at least a second type of external data to generate an RNN output. The MLP and RNN unit are collectively configured to generate one or more time series predictions based at least partially on the RNN output and the MLP output.

The MLP can include an input layer, at least one hidden layer, and an output layer. The RNN unit can include at least one hidden RNN layer. The RNN unit can include a long short-term memory RNN unit. The RNN unit can include a regular RNN unit. The RNN unit can include a gate recurrent unit.

The first type of external data can include time invariant data. The second type of external data can include time variant data.

The neural network can be configured to combine the MPL output with the RNN output to generate a residual output. The one or more time series predictions can be generated based at least partially on the residual output. The one or more time series predictions can include concentration values of a drug in plasma as a function of time following administration of a dose of the drug.

In at least one other aspect of the present disclosure, a method is provided. The method includes receiving, by a MLP, a first type of external data. The method includes processing, by the MLP, the first type of external data to generate a MLP output. The method includes receiving, by a RNN unit, at least a portion of the MLP output and a second type of external data. The method includes processing, by the RNN unit, the at least a portion of the MLP output and the second type of external data to generate an RNN output. The method includes generating one or more time series predictions based at least partially on the RNN output and the MLP output.

The first type of external data can include time invariant data. The second type of external data can include time variant data.

The method can further include combining the MPL output with the RNN output to generate a residual output. The one or more time series predictions can be generated based at least partially on the residual output. The one or more time series predictions can include concentration values of a drug in plasma as a function of time following administration of a dose of the drug.

The RNN unit can include a long short-term memory RNN unit. The RNN unit can include a regular RNN unit. The RNN unit can include a gate recurrent unit.

Implementations of the present disclosure can include one or more of the following advantages. The described neural network can process time variant data and time invariant data in a computationally efficient manner to generate accurate time series predictions, when compared to traditional neural networks, such as recurrent neural networks and convolutional neural networks. Outputs of particular neural network layers can be combined with output of successive neural network layers to enhance prediction accuracy when compared to traditional neural networks. When compared with traditional neural networks, the described neural networks can better capture the relationship between time variant data and time invariant data, and how this relationship affects a resulting time series prediction.

These and other aspects, features, and implementations can be expressed as methods, apparatus, systems, components, program products, means or steps for performing a function, and in other ways.

These and other aspects, features, and implementations will become apparent from the following descriptions, including the claims.

DETAILED DESCRIPTION

Figure 1:
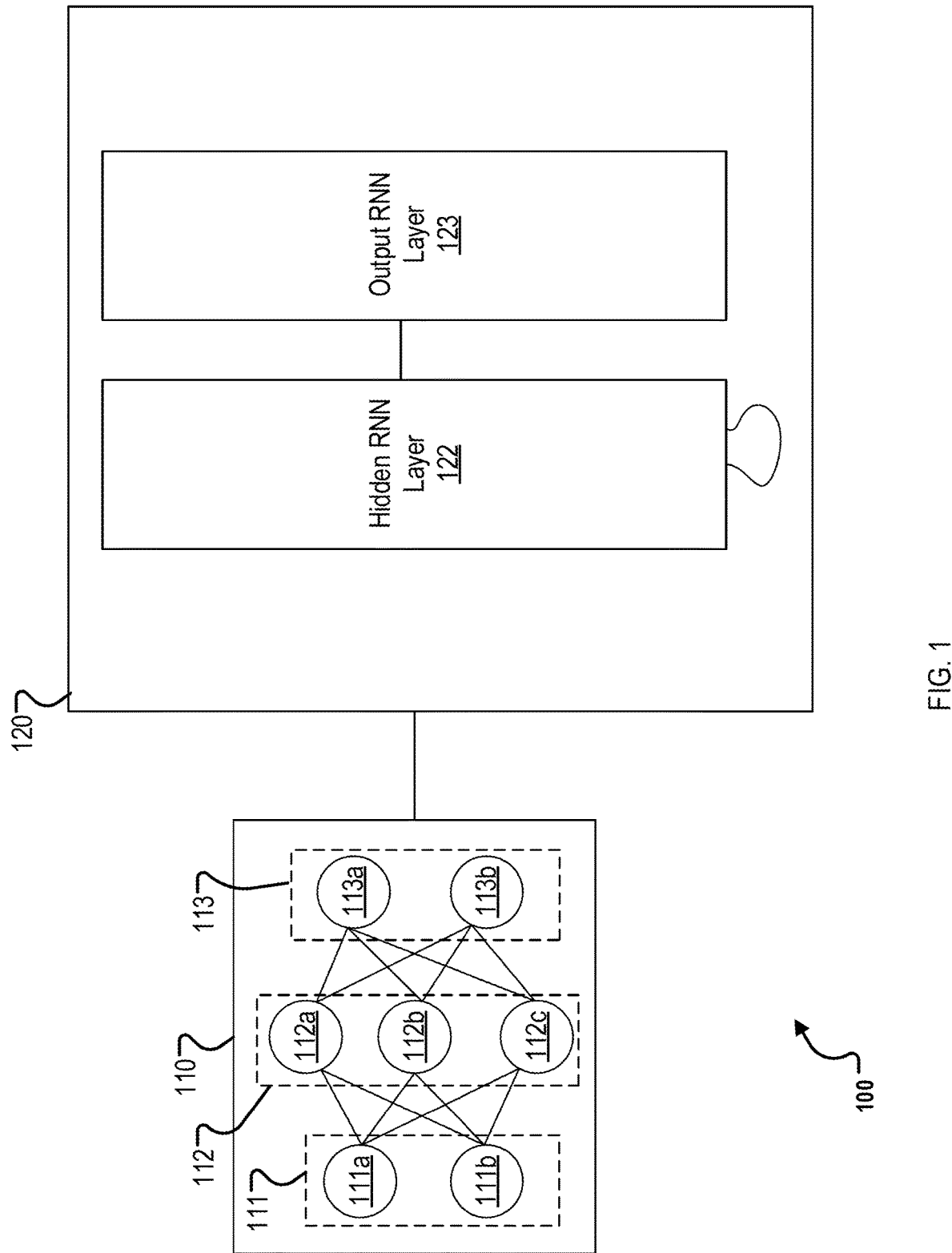
FIG. 1 shows a diagram depicting a residual semi-recurrent neural network, in accordance with one or more implementations of the present disclosure.

It is becoming more popular to use artificial neural networks (ANNs) as prediction models to predict a future outcome based on some external data. For example, pharmacokinetic (Pk) modeling is a critical step of drug development, which models how a drug interacts with the human body (e.g., the time course of drug absorption, distribution, metabolism, and excretion). In some approaches to pharmacokinetic modeling, time invariant data such as baseline characteristics of a patient (e.g., age, sex, etc), and time variant data such as dose levels of a drug in a patient, are used to generate a Pk curve that shows the concentration of the drug in the blood plasma over an interval of time. Traditionally, differential equations borrowed from the field of fluid dynamics were used to model the interactions between drug and human body. Differential equations may be useful in describing the underlying physical process occurring inside the human body after receiving a drug dose, however, differential equations may not take into account all the heterogeneities between patients. Therefore, the predictions of individual patients obtained by using these differential equations may be inaccurate while the prediction at the population level may be accurate.

General approaches to improve the prediction accuracy of pharmacokinetic modeling typically involve using feedforward neural networks (e.g., convolutional neural networks). However, although improving prediction accuracy when compared to the traditional differential equation approaches, feedforward neural networks can fail to account for the correlations between pharmacokinetic measurements at multiple time points of the same person. This is because traditional feedforward networks typically only process information in one direction (e.g., from the input layer, through hidden layers, to the output layer), and therefore feedforward networks only consider the current input without any notion of order in time.

Recurrent neural networks (RNNs) have been shown to better handle time variant data because these neural networks include nodes having connections that form a directed graph along a temporal sequence, allowing RNNs to process sequences of inputs using internal memory. However, when using conventional RNNs to process time invariant data, the RNN may treat the time invariant data in a similar manner as the time variant data. This can create a large amount of unnecessary duplicated data and result in poor prediction performance, especially when using small sample sizes. Thus, an artificial neural network adapted to efficiently process both time invariant data and time variant data to generate time based predictions with increased accuracy, when compared to traditional approaches, is desirable.

This disclosure provides residual semi-recurrent neural networks configured to process both time invariant data and time variant data in an efficient manner that improves prediction accuracy when compared to traditional RNN and feedforward networks. The residual semi-recurrent neural network includes a multilayer perceptron (MLP) for receiving and processing time invariant data. The residual semi-recurrent neural network also includes an RNN unit for processing time variant data. The outputs from the MLP and the RNN unit are used by the neural network to generate one or more time series predictions. For example, if being used for Pk modeling, the data pertaining to patient baseline characteristics are provided to the MLP, and data pertaining to the dose level of a drug given to a patient at sequential points in time is provided to the RNN. The output of the MLP can be used as the initial state of the RNN. The output of the RNN and the MLP can also be combined to generate a Pk curve showing the relationship between the concentration of a drug in the plasma of a patient and the time after a single dose of the drug has been administered to a patient.

In the following description, for the purposes of explanation, numerous specific details are set forth in order to provide a thorough understanding of the present disclosure. It will be apparent, however, that the present disclosure may be practiced without these specific details. In other instances, well-known structures and devices are shown in block diagram form in order to avoid unnecessarily obscuring the present disclosure.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all implementations or that the features represented by such element may not be included in or combined with other elements in some implementations.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Several features are described hereafter that can each be used independently of one another or with any combination of other features. However, any individual feature may not address any of the problems discussed above or might only address one of the problems discussed above. Some of the problems discussed above might not be fully addressed by any of the features described herein. Although headings are provided, data related to a particular heading, but not found in the section having that heading, may also be found elsewhere in this description.

As used herein, the term process (processing, processes, etc) used in conjunction with a given neural network layer/unit refers to the known neural network process of applying learned weights/activation functions corresponding to each of the neurons included within the given neural network layer/unit to input data to produce outputs at each neuron. As known in the art, the learned weights/activation functions can be adjusted/tuned by using training datasets to teach the neural network to associate certain features of the data sets with certain results.

System Overview:

FIG. 1 shows a diagram depicting a residual semi-recurrent neural network 100, in accordance with one or more implementations of the present disclosure. The residual semi-recurrent neural network (RSNN 100) includes a MLP 110 and a RNN unit 120. The MLP 110 includes an input layer 111, a hidden layer 112, and an output layer 113. The RNN unit 120 includes a hidden RNN layer 122 and an output RNN layer 123. The MLP 110 is communicatively coupled to the RNN unit 120.

The input layer 111 of the MLP 110 includes a first input neuron 111a and a second input neuron 111b. The hidden layer 112 of the MLP 110 includes a first hidden neuron 112a, a second hidden neuron 112b, and a third hidden neuron 112c. The output layer 113 of the MLP 110 includes a first output neuron 113a and a second output neuron 113b. The layers 111,112,113 of the MLP 110 are fully connected, meaning each neuron of a given layer is connected to every neuron in a successive layer. For example, the first output neuron 113a is connected to the first hidden neuron 112a, the second hidden neuron 112b, and the third hidden neuron 112c.

Although the MLP 110 includes one hidden layer 112, in some implementations, the MLP 110 includes more hidden layers (e.g., two hidden layers, three hidden layers, etc.). Each of the layers 111, 112, and 113 can include more or less neurons than the number of neurons shown in the illustrated implementation.

The input layer 111 is configured to receive time invariant data and send the time invariant data to the hidden layer 112. Examples of time invariant data can include values pertaining to baseline characteristics of one or more patients, such as the age and/or sex of the patients. Each of the hidden nodes 112a, 112b, 112c of the hidden layer 112 receive the time invariant data and processes the time invariant data to generate an output. The output of each of the hidden nodes 112a, 112b, 112c of the hidden layer 112 is sent to each of the output nodes 113a, 113b. The output nodes 113a, 113b process the received outputs using their activation functions to generate MLP output.

The MLP 110 sends the MLP output to the RNN unit 120. The MLP output is received by the hidden RNN layer 122. Thus, the MLP output is used as the initial state of the RNN unit 120. The hidden RNN layer 122 is also configured to receive time variant input data. As will be explained later in more detail with reference to FIG. 3, the RNN unit 120 is configured to sequentially process the received time variant data while using the MLP output from the MLP 110 as an initial state to produce one or more time series predictions. For example, the MLP output can result from processing input data associated with patient baseline characteristics, and the time invariant data can be a sequence of cumulative amounts of a drug injected into a patient. In this instances, the output of the RNN unit (the time series prediction) can be a Pk curve. In some implementations, the RSNN 100 is configured to add the MLP's 110 output to the RNN unit's 120 output to generate the time series predictions.

Although shown as having one hidden layer 122, the RNN unit 120 has additional hidden RNN layers in some implementations. In this instance, the MLP 110 can be configured to provide its output to one or more of the additional hidden RNN layers. In some implementations, the RSNN 100 includes additional fully connected layers between the MLP 110 and the RNN unit 120. In these instances, the MLP 110 can be configured to provide its output to one or more of the additional fully connected layers. The amount of additional hidden RNN layers and fully connected layers can be based on processing needs, efficiency factors, and practical considerations such as the type and amount of data being processed.

Figure 2A:
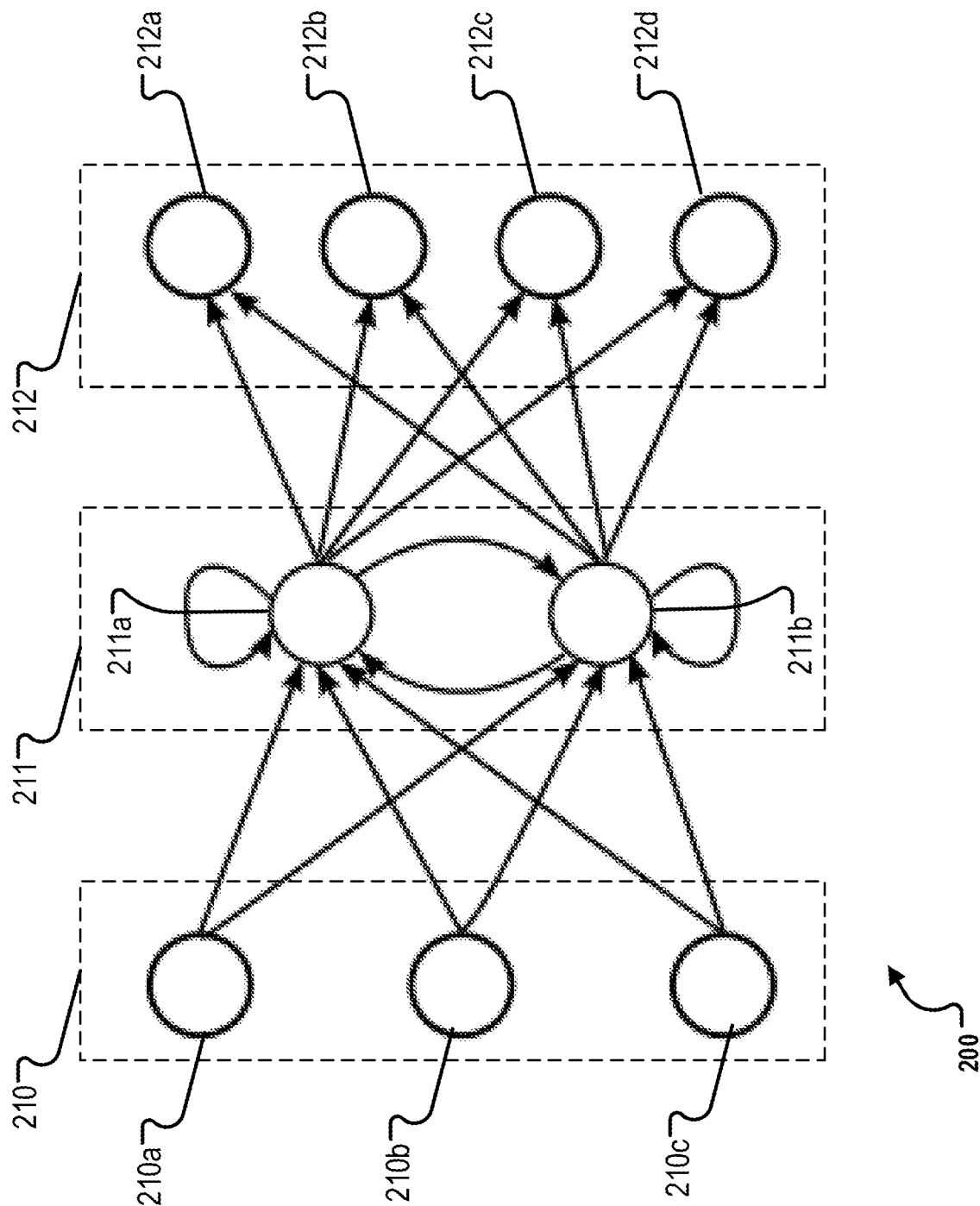
FIG. 2A shows a diagram depicting a recurrent neural network unit, in accordance with one or more implementations of the present disclosure.

FIG. 2A shows a diagram depicting a RNN unit 200, in accordance with one or more implementations of the present disclosure. The RNN unit 200 includes an input RNN layer 210, a hidden RNN layer 211, and an output RNN layer 212. The input RNN layer 210 includes a first RNN input neuron 210a, a second RNN input neuron 210b, and a third RNN input neuron 210c. In some implementations, the input RNN layer 210 is the output layer of a preceding MLP.

The hidden RNN layer 211 is configured to receive output from the input RNN layer 210. As indicated previously with reference to FIG. 1, the output from the input RNN layer can be used as an initial state for the hidden RNN layer 211. The hidden RNN layer 211 includes a first recurrent neuron 211a and a second recurrent neuron 211b. Each of the RNN input neurons 210a,210b,210c are connected to each of the recurrent neurons 211a,211b. Each of the recurrent neurons 211a,211b is configured to receive a first sequential data point, process the first sequential data point to generate a first output, and use the first output to process a successive sequential data point. For example, assume that the sequential data points are cumulative amounts of drug injected into a patient. The first sequential data point can be a cumulative amount at a first time, and a second sequential data point can be a cumulative amount at a second time occurring after the first time. The recurrent neurons 211a,211b will receive the first sequential data point, process the first sequential data point to generate a first output, and use information from the first output to process the second sequential data point.

The RNN output layer 212 is configured to receive output from the hidden layer 211. The RNN output layer 212 includes a first RNN output neuron 212a, a second RNN output neuron 212b, a third RNN output neuron 212c, and a fourth RNN output neuron 212d. Each of the RNN output neurons 212a,212b,212c,212d are connected to each of the recurrent neurons 211a,211b.

Figure 2B:
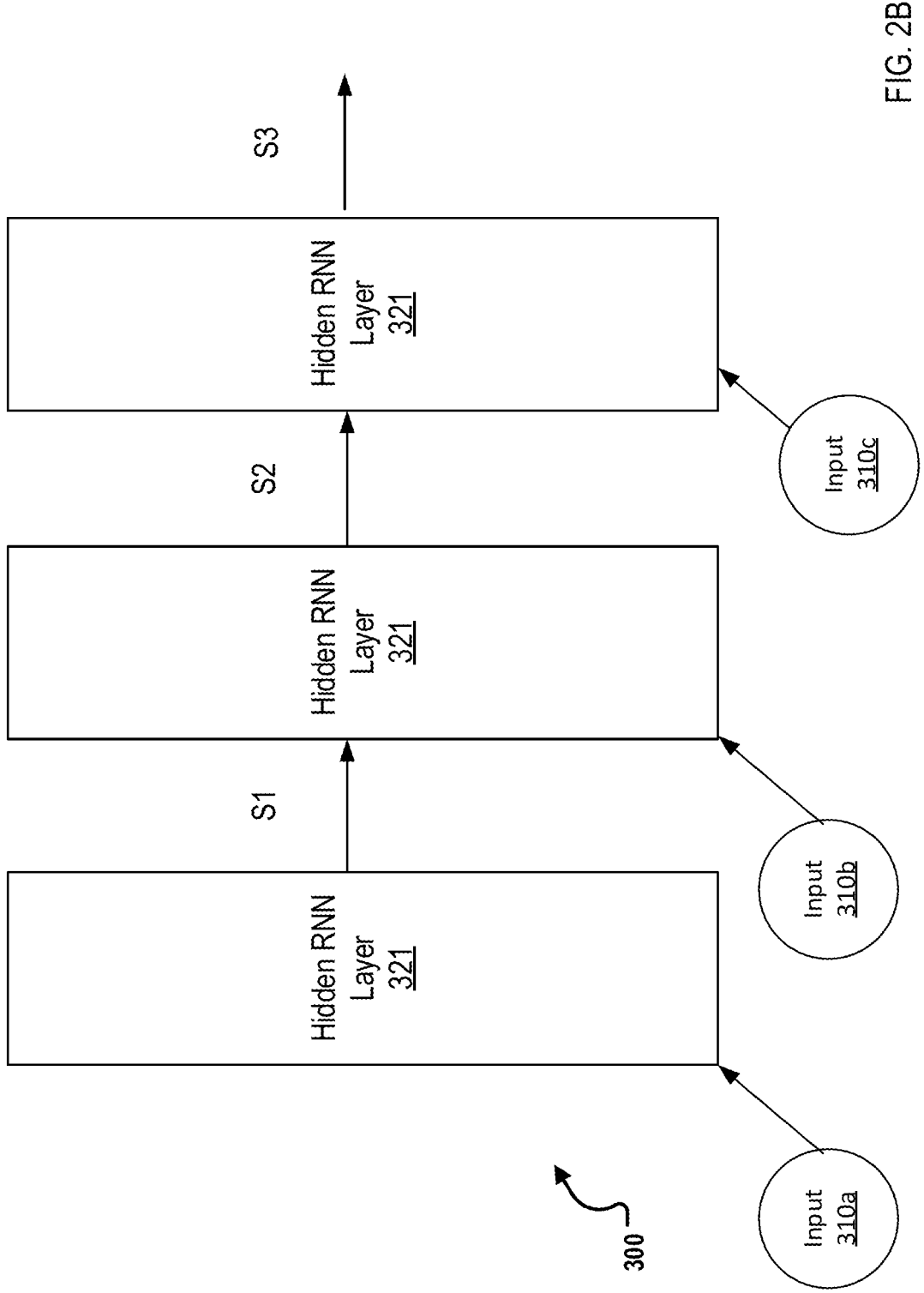
FIG. 2B shows a diagram depicting an unfolded recurrent neural network unit, in accordance with one or more implementations of the present disclosure.

FIG. 2B shows a diagram depicting an unfolded recurrent neural network unit 300, in accordance with one or more implementations of the present disclosure. As shown, the hidden RNN layer 321 is configured to receive and process a first sequential input 310a to generate a first output (S1). The hidden RNN layer 321 is also configured to receive a second sequential input 310b which follows the first sequential input 310a. The hidden RNN layer 321 uses the output (S1) associated with the first sequential input 310a to process the second sequential input 310b to generate a second output (S2). Similarly, the hidden RNN layer 321 is configured to use the second output (S2) to process a third sequential input 310c that follows the second sequential input 310b to generate a third output (S3).

Figure 3:
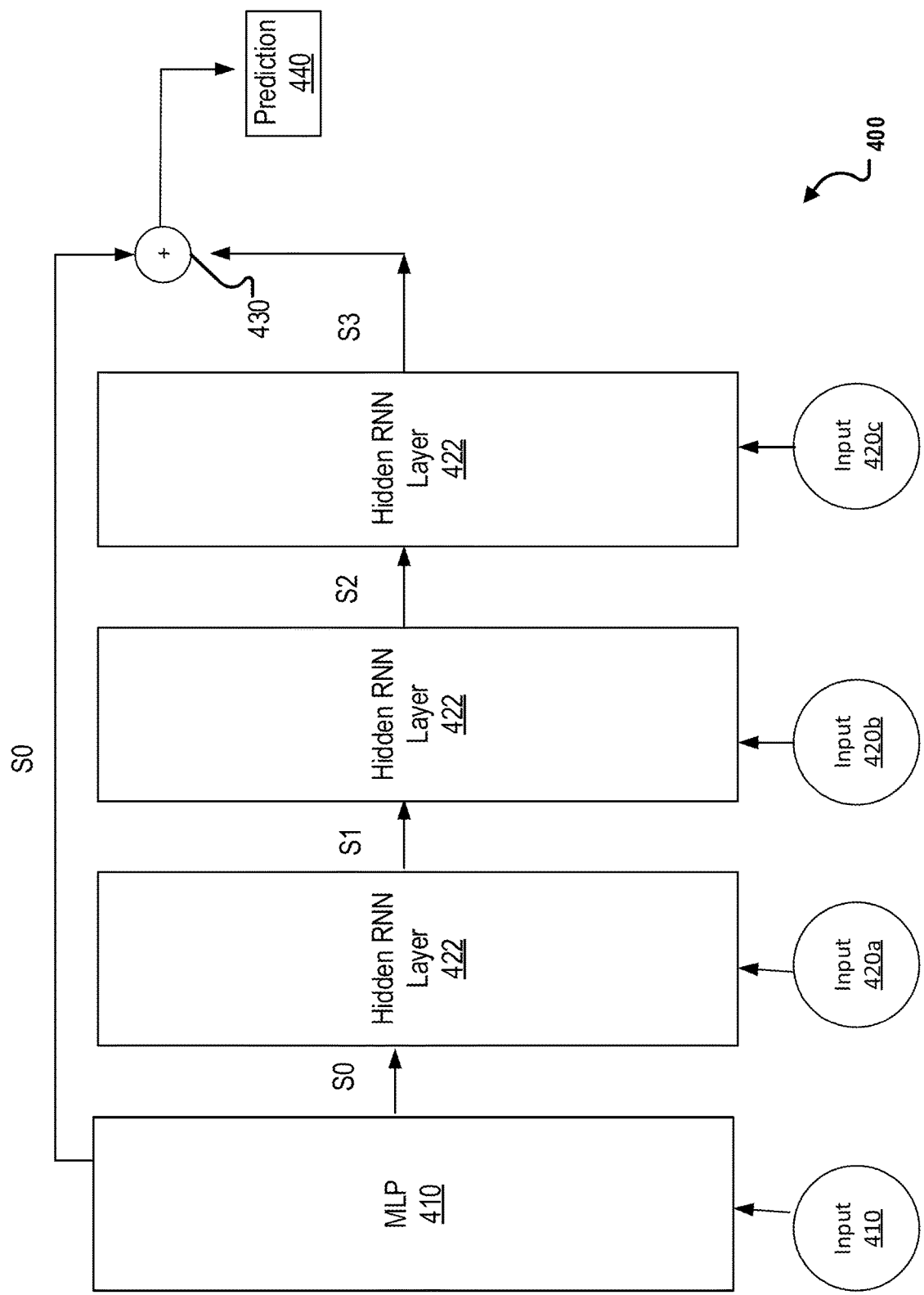
FIG. 3 is an illustration depicting an architecture of a residual semi-recurrent neural network, in accordance with one or more implementations of the present disclosure.

FIG. 3 is an illustration depicting an architecture of a RSNN 400, in accordance with one or more implementations of the present disclosure. The RSNN 400 includes an MLP 410 and a hidden RNN layer 422. The MLP 410 is configured to receive a time invariant input 410. For example, the time invariant input 410 can correspond with patient baseline characteristics, such as age, sex, and so forth. The MLP 410 processes the invariant input 410 to generate an MLP output (S0), which is used as the initial state for the hidden RNN layer 422. The Hidden RNN layer 422 receives a first sequential input 420a, and uses the MLP output (S0) to process the first sequential input 420a to generate a first RNN output (S1). The hidden RNN layer 422 then receives a second sequential input 420b and uses the first RNN output (S1) to process the second sequential input 420B and generate a second RNN output (S2). The hidden RNN layer 422 then receives a third sequential input 420c and uses the second RNN output (S2) to process the third sequential input 420c to generate a third RNN output (S3). The MLP output (S0) is then added 430 to the third RNN output (S3) to generate a time series prediction 440. In some implementations, the sequential inputs correspond to cumulative amounts of drug injected at a given time. In some implementations, the time series prediction 440 is a Pk curve.

Although the RNN units shown and described above are regular RNN units, other types of RNN units may be used. In some implementations, a long short-term memory (LSTM) RNN unit is used. A LSTM RNN unit refers to an RNN unit that includes a cell, an input gate, and output gate, and a forget gate. The cell remembers values over arbitrary time intervals and the three gates regulate the flow of information. A LSTM RNN unit can minimize the impact of the vanishing gradient problems known to be encountered in some instances when training a traditional RNN. In some implementations, a gated recurrent unit (GRU) is used as the RNN unit. A GRU is a LSTM with a forget gate but has fewer parameters than an LSTM because it lacks an output gate. When compared to an LSTM, GRUs have been shown to exhibit better prediction performance when handling relatively small datasets.

Figure 4:
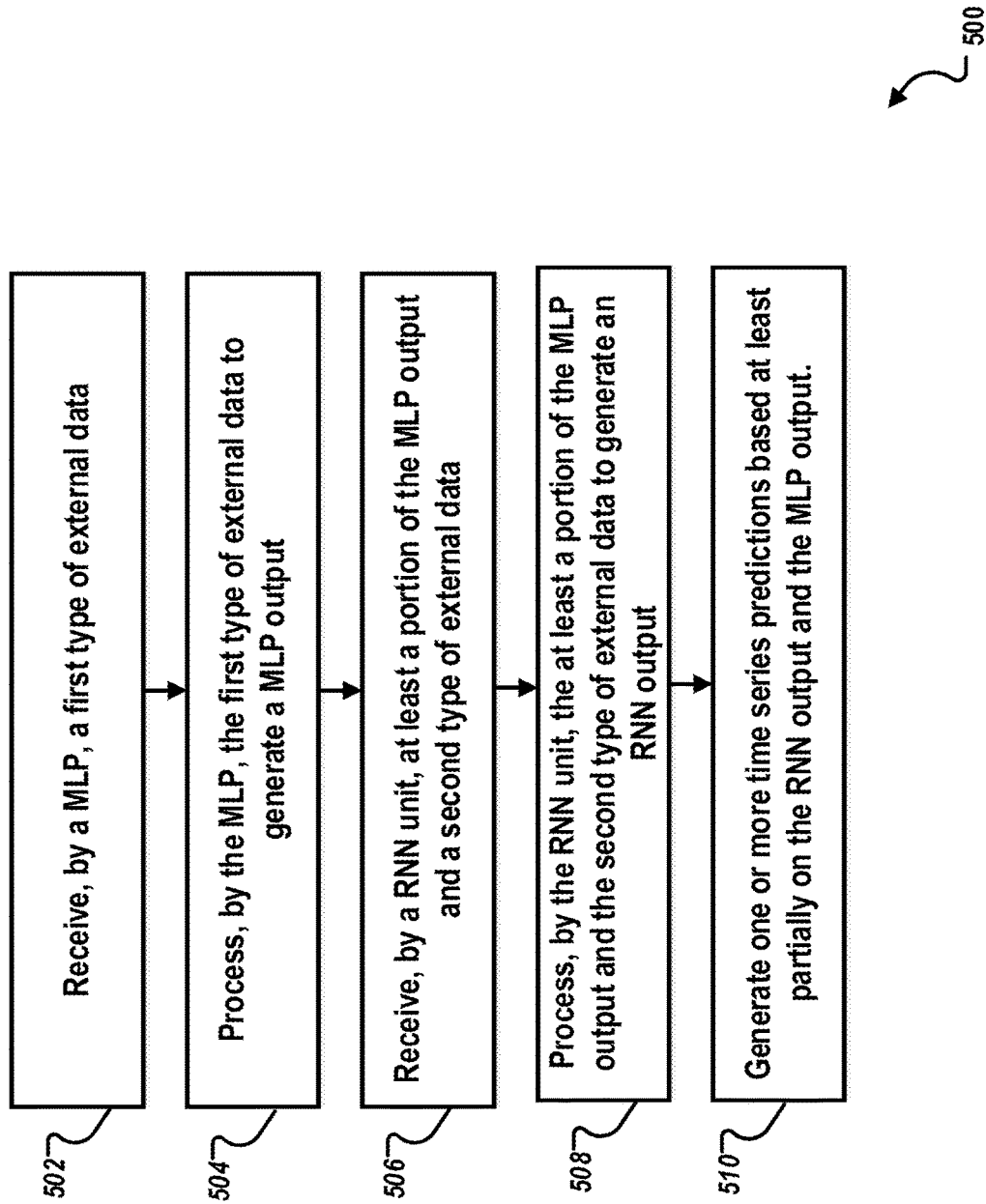
FIG. 4 is a flowchart depicting a method for generating one or more time series predictions using time variant data and time invariant data, in accordance with one or more implementations of the present disclosure.

FIG. 4 is a flowchart depicting a method 500 for generating one or more time series predictions using time variant data and time invariant data, in accordance with one or more implementations of the present disclosure. The method 500 includes receiving, by an MLP, a first type of external data (block 502); processing, by the MLP, the first type of external data to generate a MLP output (block 504); receiving, by a RNN unit, at least a portion of the MLP output and a second type of external data (block 506); processing, by the RNN unit, at least a portion of the MLP output and the second type of external data to generate an RNN output (block 508); and generating one or more time series predictions based at least partially on the RNN output and the MLP output.

At block 502, the MLP of the RSNN receives a first type of external data. In some implementations, the first type of external data is time invariant data. For example, the time invariant data can be baseline patient characteristics.

At block 504, the MLP processes the first type of external data to generate an MLP output as previously described with reference to FIG. 1.

At block 506, the RNN unit of the MLP receives at least a portion of the MLP output from the MLP. The RNN unit also receives a second type of external data. In some implementations, the second type of external data is time variant data. For example, the time variant data can be a sequence of cumulative amounts of a drug injected into a patient.

At block 508, the RNN unit processes the received portions of the MLP output, along with the second type of external data, to generate an RNN output as previously described with reference to FIG. 3.

At block 510, the RSNN generates one or more time series predictions based at least partially on the RNN output and the MLP output. In some implementations, the RSNN combines the RNN output with the MLP output to generate the one or more time series predictions. A time series prediction can be, for example, a Pk curve.

Example Method of Training a RSNN

An example method for training an RSNN for pharmacokinetic modeling will now be described. A RSNN is trained and validated as a pharmacokinetic model $\hat{f}$ using the output and input pair, $$\{y_i, \tilde{x}_i\}_{i=1}^k,$$

where $\tilde{x}_i = (x_i, d_i)$ are the inputs to the model. The variable $x_i$ is a p-dimensional vector representing the p baseline characteristics of the ith patient and $d_i$ is the time sequence of actual dose levels assigned to the ith patient. The variable $y_i$ represents the output from the model, that is, the time sequence of observed pharmacokinetic concentration of the ith patient. The model is iteratively trained using patients from a training set. During the training process, the model compares its generated prediction $c_i$ against the ground-truth data $c_i$, and updates its weight's accordingly.

When the model is trained $\hat{\varphi}$, for a given instance i, the sequence of inputs includes $$\{(x_{it}, d_{it})\}_{t=i}^{T_i} \text{ and } \{(x_{it}, d_{it}, c_{it})\}_{t=1}^{T_i}$$

respectively, where $x_{i1} = x_{i2} = x_{i3}, \ldots, = x_{iT_i}$ does not change over time because they are time invariant baseline characteristics.

The baseline characteristics are provided to the multilayer perceptron (MLP) of the RSNN. Then the output of the MLP is used as the initial state of the traditional RNN unit of the RSNN. The time-variant data (e.g., the dose levels assigned to a patient and a given time) is provided to the traditional RNN unit. Because it is possible that the time-invariant inputs are more influential on the Pk model than the time-variant inputs, a shortcut connection between the MLP used to handle the time-invariant inputs and the fully-connected layers stacked on top of the recurrent layers is implemented. This shortcut provides a means to directly propagate the information contained in the time-invariant inputs to the final output of the RNN unit.

Mathematically, the RSNN is defined as follows. For a given instance i, the time-invariant input $x_i$ and a sequence of time-variant inputs $(z_{i1}, z_{i2}, \ldots, z_{iT_i})$, the sequence of outputs $\hat{y}_{it} = f^{RS}(x_i, z_{i1}, z_{i2}, \ldots, z_{iT_i})$ is obtained by $$s_{i0} = \sigma(Tx_i + c), \tag{1}$$

$$s_{it} = \sigma(Uz_{it} + Ws_{i,t-1} + b), t = 1, \ldots, T_i, \tag{2}$$

$$\hat{y}_{it} = \sigma(Vs_{it} + a) + Ps_{i0}, t = 1, \ldots, T_i, \tag{3}$$

where the first equation (1) defines a fully-connected layer for the MLP. The parameters $x_i \in \mathbb{R}^k$, $z_{it} \in \mathbb{R}^p$, $s_{it} \in \mathbb{R}^q$, $\hat{y}_{it} \in \mathbb{R}^r$ and $T \in \mathbb{R}^{q \times k}$, $c \in \mathbb{R}^q$, $U \in \mathbb{R}^{q \times p}$, $W \in \mathbb{R}^{q \times q}$, $b \in \mathbb{R}^q$, $V \in \mathbb{R}^{r \times q}$, $a \in \mathbb{R}^r$, $P \in \mathbb{R}^{r \times q}$ are the parameters to be trained.

For modeling pharmacokinetics, the relationship $z_{it} = d_{it}$ is used. Similarly, the MLP may contain more than one fully-connected layers. In addition, when there are more than one recurrent layers in the RNN unit, the initial states of the first recurrent layer only, the last recurrent layer only, or all the recurrent layers may be be the output of the MLP. Additionally, when there are more than one fully-connected layers tacked on top of the recurrent layers, the output of the MLP may be provided to the first fully-connected layer only, the last fully-connected layer only, or all the fully-connected layers. These different design decisions may be considered hyperparameters.

Experimental Results:

A dataset consisting of 65 patients was provided to an example RSNN that used a gated recurrent neural network (GRU) as the RNN unit. For each patient, a sequence of observed PK values ($y_i$), two baseline characteristics ($x_i$)—age and sex, and a sequence of cumulative amounts of drug injected ($d_i$) was used. A GRU was used to connect inputs and outputs at each time point of the RSNN for the dataset, and results (e.g., Pk curves) of the training and validation sets were fitted.

The RSNN model accurately fit all the PK curves in the validation set, including two PK curves with very high peaks that were seen in the training set. This indicated that the RSNN was able to capture the complex nonlinear relationship between the PK values and the cumulative amounts of drug injected, as well as the baseline characteristics.

In the foregoing description, implementations of the disclosure have been described with reference to numerous specific details that may vary from implementation to implementation. The description and drawings are, accordingly, to be regarded in an illustrative rather than a restrictive sense. The sole and exclusive indicator of the scope of the disclosure, and what is intended by the applicants to be the scope of the disclosure, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising," in the foregoing description or following claims, what follows this phrase can be an additional step or entity, or a sub-step/sub-entity of a previously-recited step or entity.

What is claimed is:

1. A method performed by one or more computers, the method comprising:
    receiving data characterizing a subject, the data comprising:
        (i) a sequence of time-varying features of the subject, wherein the sequence of time-varying features includes a respective time-varying feature of the subject for each time point in a sequence of time points; and
        (ii) a set of time-invariant features of the subject, wherein the time-invariant features of the subject are the same for each time point in the sequence of time points;
    processing the set of time-invariant features of the subject using a multilayer perceptron to generate an encoded representation of the set of time-invariant features of the subject;
    processing the sequence of time-varying features of the subject using a recurrent neural network to generate an encoded representation of the sequence of time-varying features of the subject, comprising, for each time point in the sequence of time points:
        processing the time-varying feature of the subject for the time point and a hidden state of the recurrent neural network to update the hidden state of the recurrent neural network;
    generating a combined feature representation by combining: (i) the encoded representation of the set of time-invariant features of the subject generated by the multilayer perceptron, and (ii) the encoded representation of the set of time-varying features of the subject generated by the recurrent neural network; and
    processing the combined feature representation to generate one or more predictions characterizing the subject.

2. The method of claim 1, wherein the multilayer perceptron and the recurrent neural network are trained on a set of training data that includes training examples corresponding to fewer than 65 subjects.

3. The method of claim 1, wherein the recurrent neural network comprises one or more gated recurrent neural network units.

4. The method of claim 1, wherein the subject is a patient.

5. The method of claim 1, further comprising, prior to processing the sequence of time-varying features of the subject using the recurrent neural network:
    initializing a hidden state of the recurrent neural network based on the encoded representation of the set of time-invariant features of the subject.

6. The method of claim 1, wherein the encoded representation of the set of time-varying features of the subject is based on the hidden state of the recurrent neural network.

7. The method of claim 1, wherein for each time point in the sequence of time points, the time-varying feature of the subject for the time point characterizes a dosage level of a drug that is administered to the subject at the time point.

8. The method of claim 7, wherein for each time point in the sequence of time points, the time-varying feature of the subject for the time point characterizes a cumulative dosage of the drug administered to the subject as of the time point.

9. The method of claim 1, wherein the sequence of time points comprises a first time point and a second time point, wherein the time-varying feature of the subject has a first value at the first time point and a second, different value at the second time point.

10. The method of claim 1, wherein the one or more predictions characterizing the subject comprise pharmacokinetic modeling predictions.

11. The method of claim 10, wherein the pharmacokinetic modeling predictions comprise, for each time point in the sequence of time points, a predicted concentration value of a drug in blood of the subject at the time point.

12. The method of claim 1, wherein the set of time-invariant features of the subject comprise a feature characterizing an age of the subject.

13. The method of claim 1, wherein the set of time-invariant features of the subject comprise a feature characterizing a sex of the subject.

14. The method of claim 1, wherein the multilayer perceptron comprises multiple hidden layers.

15. The method of claim 1, wherein generating a combined feature representation by combining: (i) the encoded representation of the set of time-invariant features of the subject generated by the multilayer perceptron, and (ii) the encoded representation of the set of time-varying features of the subject generated by the recurrent neural network comprises:
summing: (i) the encoded representation of the set of time-invariant features of the subject generated by the multilayer perceptron, and (ii) the encoded representation of the set of time-varying features of the subject generated by the recurrent neural network.

16. The method of claim 1, wherein the recurrent neural network comprises a long short-term memory neural network layer.

17. The method of claim 1, wherein the recurrent neural network and the multilayer perceptron are jointly trained by a machine learning training technique.

18. The method of claim 1, wherein for each time point in the sequence of time points, the time-varying feature of the subject for the time point characterizes a dosage level of a drug that is administered to the subject at the time point; and
wherein the one or more predictions characterizing the subject comprise pharmacokinetic modeling predictions.

19. The method of claim 18, wherein the pharmacokinetic modeling predictions comprise, for each time point in the sequence of time points, a predicted concentration value of a drug in blood of the subject at the time point.

20. The method of claim 19, further comprising, prior to processing the sequence of time-varying features of the subject using the recurrent neural network:
initializing a hidden state of the recurrent neural network based on the encoded representation of the set of time-invariant features of the subject.

21. The method of claim 20, wherein the recurrent neural network and the multilayer perceptron are jointly trained by a machine learning training technique.

22. The method of claim 21, wherein for each time point in the sequence of time points, the time-varying feature of the subject for the time point characterizes a cumulative dosage of the drug administered to the subject as of the time point;
wherein the multilayer perceptron and the recurrent neural network are trained on a set of training data that includes training examples corresponding to fewer than 65 subjects;
wherein the encoded representation of the set of time-varying features of the subject is based on the hidden state of the recurrent neural network.

23. The method of claim 22, wherein the set of time-invariant features of the subject comprise a feature characterizing an age of the subject;
wherein the set of time-invariant features of the subject comprise a feature characterizing a sex of the subject; and
wherein generating a combined feature representation by combining: (i) the encoded representation of the set of time-invariant features of the subject generated by the multilayer perceptron, and (ii) the encoded representation of the set of time-varying features of the subject generated by the recurrent neural network comprises:
summing: (i) the encoded representation of the set of time-invariant features of the subject generated by the multilayer perceptron, and (ii) the encoded representation of the set of time-varying features of the subject generated by the recurrent neural network.

24. A system comprising:
one or more computers; and
one or more storage devices communicatively coupled to the one or more computers, wherein the one or more storage devices store instructions that, when executed by the one or more computers, cause the one or more computers to perform operations comprising:
receiving data characterizing a subject, the data comprising:
(i) a sequence of time-varying features of the subject, wherein the sequence of time-varying features includes a respective time-varying feature of the subject for each time point in a sequence of time points; and
(ii) a set of time-invariant features of the subject, wherein the time-invariant features of the subject are the same for each time point in the sequence of time points;
processing the set of time-invariant features of the subject using a multilayer perceptron to generate an encoded representation of the set of time-invariant features of the subject;
processing the sequence of time-varying features of the subject using a recurrent neural network to generate an encoded representation of the sequence of time-varying features of the subject, comprising, for each time point in the sequence of time points:
processing the time-varying feature of the subject for the time point and a hidden state of the recurrent neural network to update the hidden state of the recurrent neural network;
generating a combined feature representation by combining: (i) the encoded representation of the set of time-invariant features of the subject generated by the multilayer perceptron, and (ii) the encoded representation of the set of time-varying features of the subject generated by the recurrent neural network; and
processing the combined feature representation to generate one or more predictions characterizing the subject.

25. One or more non-transitory computer storage media storing instructions that when executed by one or more computers cause the one or more computers to perform operations comprising:
receiving data characterizing a subject, the data comprising:
(i) a sequence of time-varying features of the subject, wherein the sequence of time-varying features includes a respective time-varying feature of the subject for each time point in a sequence of time points; and
(ii) a set of time-invariant features of the subject, wherein the time-invariant features of the subject are the same for each time point in the sequence of time points;
processing the set of time-invariant features of the subject using a multilayer perceptron to generate an encoded representation of the set of time-invariant features of the subject;

processing the sequence of time-varying features of the subject using a recurrent neural network to generate an encoded representation of the sequence of time-varying features of the subject, comprising, for each time point in the sequence of time points:
  processing the time-varying feature of the subject for the time point and a hidden state of the recurrent neural network to update the hidden state of the recurrent neural network;
generating a combined feature representation by combining: (i) the encoded representation of the set of time-invariant features of the subject generated by the multilayer perceptron, and (ii) the encoded representation of the set of time-varying features of the subject generated by the recurrent neural network; and
processing the combined feature representation to generate one or more predictions characterizing the subject.

* * * * *